United States Patent [19]

Dudkowski

[11] Patent Number: 4,786,632

[45] Date of Patent: Nov. 22, 1988

[54] EMULSIFIABLE CONCENTRATES OF MALATHION WITH INHERENT LOW EYE-IRRITATION PROPERTIES

[75] Inventor: Joseph J. Dudkowski, Bridgewater, N.J.

[73] Assignee: American Cyanamid Company, Stamford, Conn.

[21] Appl. No.: 529,671

[22] Filed: Sep. 6, 1983

Related U.S. Application Data

[63] Continuation-in-part of Ser. No. 426,431, Sep. 29, 1982, abandoned.

[51] Int. Cl.$^4$ .............................................. H01N 57/00
[52] U.S. Cl. ..................................... 514/122; 514/975
[58] Field of Search .......................... 424/213; 514/122

[56] References Cited

U.S. PATENT DOCUMENTS

| | | | |
|---|---|---|---|
| 3,197,299 | 7/1965 | Stull et al. | 424/213 X |
| 3,396,223 | 8/1968 | Stark | 424/200 |
| 3,515,782 | 6/1970 | Nolan | 424/213 |
| 3,911,121 | 10/1975 | Roberts | 424/219 |

*Primary Examiner*—Leonard Schenkman
*Attorney, Agent, or Firm*—Estelle J. Tsevdos

[57] ABSTRACT

Emulsifiable concentrates of malathion having low eye irritation properties. Compositions of the invention yield stable emulsions when diluted with water.

2 Claims, No Drawings

EMULSIFIABLE CONCENTRATES OF MALATHION WITH INHERENT LOW EYE-IRRITATION PROPERTIES

This application is a continuation-in-part of application Ser. No. 426,431, filed Sept. 29, 1982.

The invention herein described relates to emulsifiable concentrates of malathion which have low eye irritation properties. These malathion concentrates form stable emulsions when diluted with water.

By way of background, the phosphorodithioate insecticide known commercially as malathion[S-1,2-bis-ethoxycarbonyl)ethyl 0,0-dimethyl phosphorodithioate] is a well-known and valuable insecticide which is especially useful for the control of aphids, mosquitoes, mediterrean fruit flies and a variety of other outdoor and household insects. Malathion is described in U.S. Pat. No. 2,578,652. A process for reducing the objectionable odor of this malodorous phosphorodithioate is described in U.S. Pat. No. 2,980,723. Variously used patents involving malathion are known (i.e., U.S. Pat. Nos. 3,352,664; 3,396,223; and 3,515,782). These patents are incorporated herein by way of reference.

Among the most commonly available commercial formulations of malathion, the emulsifiable concentrates are preferred. These formulations usually comprise on a weight basis about 30 to 70% malathion, about 3 to 10% of a surfactant or blends of surfactants, and the balance of the formulations is usually an inert aromatic solvent or other suitable solvent having a low order of toxicity. However, almost all of these formulations cause irreversible damage to mammalian eye tissue (usually corneal damage) following accidental or purposeful eye exposure. It is believed that eye damage is causally related to the surfactant(s) used in these formulations, rather than either the malathion or the solvent components.

In light of the foregoing summary of limitations of conventional formulations of malathion, an improved composition of this insecticide having diminished eye irritation properties is highly desirable. Accordingly, an object of this invention is to provide new and useful compositions of malathion having low eye irritation characteristics. This object is manifest in the following description and particularly delineated in the appended claims.

It has been unexpectedly discovered that certain emulsifiable compositions of the present inventions are inherently safer to use than are other commercially available emulsifiable concentrates of malathion. Eye irritation which may occur from exposure to formulations of the invention is temporary and usually clears up in about five to twelve days without permanently scarring eye tissue.

Conveniently, formulations of the invention can be prepared by mixing on a weight basis about 30 to 70% (preferably 50 to 63%) malathion with about 1 to 5% (preferably 2.1 to 4.2%) TOXIMUL ®475, and about 0.5 to 3.5% (preferably 1.4 to 2.8%) of TOXIMUL ®480; the remainder of the formulation is a solvent selected from xylene or a heavy aromatic naphtha (i.e., a mixture consisting primarily of xylene, methyl-ethylbenzene and trimethyl benzene). The thus obtained mixture is agitated, with a mild heating if so desired, until a clear solution forms. TOXIMUL ®475 and TOXIMUL ®480 are both liquid blends of anionic and nonionic surfactants manufactured by the Stepan Chemical Company. These products consist of blends of calcium dodecylbenzene sulfonate and mixtures of alkylphenoxy polyoxyethylene ethanols and polyalkylene glycol ether nonionic surfactants. The physical characteristics and gas chromatographic profiles of TOXIMUL ®475 and 480 are included herein for identification of these surfactant blends.

The emulsifiable malathion concentrates of the present invention cause only reversible eye irritation in mammals. Irritation clears up within about five to twelve days after exposure without permanently scarring eye tissue. In contrast, almost all conventional formulations of malathion unfortunately cause irreversible eye damage.

The following Examples further serve to illustrate the invention and are not intended to be limitative thereof.

EXAMPLE 1

Preparation of emulsifiable concentrates of malathion for eye irritation studies Malathion, a selected aromatic solvent and one or more emulsifiers are mixed. The mixture is then stirred and heated, if necessary, until a homogeneous solution forms. The percent by weight of unique components of emulsifiable concentrates prepared in this manner is given in Table I below. Table I also shows data on eye irritation as well as on emulsion and storage stability of various formulations. Samples thus prepared are stored at 25° C. and at 45° C. respectively, and are sampled periodically for emulsion stability and eye irritation tests.

Emulsion Stability Tests (WHO)

Standard hard water is prepared by dissolving anhydrous calcium chloride (0.304 g) and magnesium chloride hexahydrate (0.139 g) in distilled water. The volume is adjusted to one liter to yield water with a hardness of 342 ppm calculated as calcium carbonate.

Standard hard water (75 to 80 ml) is added to a 250 ml beaker having an internal diameter of 6 to 6.5 cm and a 100 ml calibration mark; both water and beaker are maintained at 30±1° C. The water is stirred at about 240 rpm while the required amount of emulsifiable concentrate is added via a pipette, with the flow of the concentrate being directed towards the center of the beaker. While stirring, the volume of the emulsion is adjusted to 100 ml with standard hard water and is immediately poured into a 100 ml graduated cylinder. The sample is maintained at 29° to 31° C. for one hour and examined for any creaming or separation. In this context creaming is defined as the formulation at the top or bottom of the emulsion of a layer containing a proportion of the dispersed phase greater than that in the remainder of the emulsion. An emulsion prepared from 5 ml concentrate and 95 ml standard hard water is regarded as acceptable if any separation, including creaming at the top and sedimentation at the bottom, does not exceed 2 ml.

Eye irritation is tested by introducing a 0.1 ml sample of the emulsifiable concentrate into the conjunctival sac of male albino rabbits. Each test is replicated six times and the data obtained are averaged. Daily observations are made until it is established that the irritation produced by the sample is reversible or irreversible. The scoring used to determine eye irritation reactions is described by Draize, J. H., et al., J. Pharmacol. Exptl. Therap., 82: 377 (1944).

Various emulsifiers, which are designated by lower case letters and are so identified in Table I below, are employed in the preparation of emulsifiable concentrates. These emulsifiers are identified by their commerical names, available physical constants, and by gas chromatograms taken with a Hewlett Packard Model 5710 instrument equipped with an automatic liquid sampler and standard flame ionization detector. Integration and reports are generated by a Hewlett Packard Model 3354 computer system. Chromatography was performed using the following column and conditions: 6 ft×2 mm I.D. glass column, packed with 80/100 mesh Carbopack C/0.1% SP-1000 (Supelco Cat. No. 1-1820).

| | |
|---|---|
| Column temperature | 180° C. |
| Injection port | 230° C. |
| Detector | 300° C. |
| Carrier gas (nitrogen) flow | 30 ml/min. |

Results are given as specific responses (area: wt in mg) at various retention times.

a=TOXIMUL®475. This emulsifier is a liquid blend of anionic and nonionic surfactants which is manufactured by Stepan Chemical Company. TOXIMUL®475 has a specific gravity of 0.98 at 25° C.; flash point (T.O.C. °F.)=125; flash point (closed cup)=71° F.; pH=6.0-6.2 (of a 5% solution in 50/50 2-propanol/water) lbs/gal at 250° C.=8.18; viscosity at 25° C.=200 cps; and the following gas chromatography characteristics:

| Retention time (min.) | Specific response |
|---|---|
| 1.38 | 110.5 |
| 1.73 | 38.1 |
| 1.83 | 52.1 |
| 2.21 | 40.5 |
| 4.19 | 1505.2 |
| 7.32 | 446.8 |
| 10.41 | 20.9 |
| 13.82 | 1260.1 |
| 15.30 | 549.9 |
| 34.51 | 15.2 | b=TOXIMUL®480. This emulsifier is a liquid blend of anionic and nonionic surfactants which is manufactured by Stepan Chemical Company. TOXIMUL®480 has a specific gravity at 1.001 at 25° C.; flash point (T.O.C. °F.)=125; flash point (closed cup)=68° F.: pH=5.0 (5% solution in 50/50 2-propanol/water); lbs/gal at 25° C.=8.35; viscosity at 25° C.=200 cps; and the following gas chromatography characteristics:

| Retention time (min.) | Specific response |
|---|---|
| 1.69 | 26.7 |
| 2.21 | 44.5 |
| 4.15 | 1068.0 |
| 5.76 | 9.8 |
| 7.33 | 411.4 |
| 10.39 | 22.3 |
| 13.85 | 1231.4 |
| 15.35 | 544.6 |
| 17.65 | 13.1 |
| 18.67 | 24.6 |
| 20.90 | 15.1 |
| 27.81 | 27.3 | c=Triton AG 190. This emulsifier is a liquid blend of alkyl polyether alcohol with organic sulfonates which is manufactured by Rohm and Haas Company. Triton AG 190 has a specific gravity of 1.10 at 25° C.; flash point (Seta flash C.C.)> +79° C.; pH=7 (5% aqueous); and the following gas chromatography characteristics:

| Retention time (min.) | Specific response |
|---|---|
| 13.90 | 0.5 |
| 15.37 | 8.3 |
| 44.94 | 529.2 | d=Triton AG 193. This emulsifier is a liquid blend of dodecylbenzene sulfonate and ethoxylated nonylphenol which is manufactured by Rohm and Haas Company. Triton AG 193 has a specific gravity of 1.10; flash point (Seta flash C.C.)> +79° C.; pH=7 (5% aqueous); and the following gas chromatography characteristics:

| Retention time (min.) | Specific response |
|---|---|
| 7.24 | 6.4 |
| 10.03 | 14.5 |
| 13.71 | 24.6 |
| 15.12 | 316.9 |
| 17.08 | 80.9 |
| 23.78 | 294.3 |
| 26.03 | 240.5 |
| 46.61 | 181.3 |
| 57.43 | 462.0 | e=T-MULZ 1450-H. This emulsifier is a liquid blend of nonionic and anionic surfactants which is manufactured by Thompson-Hayward Chemical Company. T-MULZ 1450-H has a specific gravity of 0.996 at 20° C.; flash point (Pensky Martin C.C.) −13° C.; pH=5-7 (1% aqueous dispersion); and the following gas chromatography characteristics:

| Retention time (min.) | Specific response |
|---|---|
| 2.23 | 67.0 |
| 7.39 | 172.4 |
| 10.22 | 5.4 |
| 13.96 | 884.5 |
| 15.44 | 837.3 |
| 24.34 | 19.4 |
| 26.65 | 10.9 |
| 46.59 | 267.9 | f=Polyfac 4754-91N. This emulsifier is a liquid surfactant which is manufactured by Westvaco Chemical Division. Polyfac 4754-91N has a specific gravity of 1.04 at 25° C.; flash point (PMCC) +56° C.; pH=5-7 (1% aqueous); and the following gas chromatography characteristics:

| Retention time (min.) | Specific response |
|---|---|
| 16.59 | 184.3 |
| 23.71 | 45.8 |
| 33.76 | 492.6 |
| 38.74 | 238.8 |
| 42.88 | 308.6 |
| 46.15 | 842.7 | g=Polyfac 4754-91A. This emulsifier is a liquid surfactant which is manufactured by Westvaco Chemical Division. Polyfac 4754 has a specific gravity of 1.03 at 25° C.; flash point (PMCC) +56° C.; pH 5-7 (1% aqueous); and the following gas chromatography characteristics:

| Retention time (min.) | Specific response |
| --- | --- |
| 17.03 | 206.6 |
| 23.97 | 45.9 |
| 34.41 | 608.3 |
| 39.31 | 257.4 |
| 43.06 | 205.2 |
| 46.64 | 41.3 |
| 57.29 | 150.9 | h=Sponto 140-T. This emulsifier is a liquid blend of polyoxyethylene ethers and oil-soluble sulfonates which is manufactured by Witco Chemical Corporation and has the following gas chromatography characteristics:

| Retention time (min.) | Specific response |
| --- | --- |
| 7.23 | 5.6 |
| 10.02 | 12.9 |
| 13.71 | 30.5 |
| 15.11 | 266.5 |
| 16.24 | 425.2 |
| 17.23 | 341.5 |
| 18.09 | 269.6 |
| 23.78 | 310.6 |
| 26.05 | 249.9 |
| 29.01 | 6.5 |
| 41.92 | 10.4 |
| 46.68 | 193.7 |
| 57.54 | 547.7 | i=Sponto 31-14L. This emulsifier is a liquid blend of anionic and nonionic surfactants which is manufactured by Witco Chemical Corporation and has the following gas chromatography characteristics:

| Retention time (min.) | Specific response |
| --- | --- |
| 7.26 | 11.6 |
| 10.05 | 18.1 |
| 13.74 | 52.2 |
| 15.16 | 276.5 |
| 16.43 | 385.0 |
| 17.27 | 469.2 |
| 18.14 | 341.9 |
| 23.84 | 423.0 |
| 26.11 | 322.8 |
| 29.09 | 9.8 |
| 42.06 | 29.6 |
| 46.77 | 26.8 |
| 57.62 | 288.6 | j=Sponto 31-14H. This emulsifier is a liquid blend of anionic and nonionic surfactants manufactured by Witco Chemical Corporation and has the following gas chromatography characteristics:

| Retention time (min.) | Specific response |
| --- | --- |
| 1.71 | 16.3 |
| 7.31 | 11.0 |
| 10.12 | 15.3 |
| 13.84 | 50.5 |
| 15.27 | 242.6 |
| 17.27 | 425.6 |
| 18.25 | 141.5 |
| 24.02 | 360.5 |
| 26.29 | 273.6 |
| 29.28 | 6.4 |
| 42.36 | 22.6 |
| 47.04 | 215.4 |
| 57.95 | 511.1 | k=Atlox 3423. This emulsifier is a liquid blend of anionic and nonionic surfactants which is manufactured by ICI United States Incorporated and has the following gas chromatography characteristics:

| Retention time (min.) | Specific Response |
| --- | --- |
| 2.19 | 77.2 |
| 14.94 | 105.4 |
| 18.03 | 6.0 |
| 23.23 | 108.9 |
| 26.01 | 19.4 |
| 31.59 | 329.8 |
| 36.09 | 255.1 |
| 41.66 | 144.7 |
| 45.42 | 7.8 |
| 47.44 | 7.8 |
| 55.72 | 178.7 | l=Atlox 3424. This emulsifier is a liquid blend of anionic and nonionic surfactants which is manufactured by ICI United States Incorporated.

m=Atlox 3426. This emulsifier is a liquid blend of anionic and nonionic surfactants which is manufactured by ICI United States Incorporated and has the following gas chromatography characteristics:

| Retention time (min.) | Specific response |
| --- | --- |
| 2.21 | 66.3 |
| 15.29 | 96.0 |
| 17.18 | 12.9 |
| 18.21 | 8.1 |
| 23.75 | 153.4 |
| 26.43 | 47.6 |
| 32.55 | 254.7 |
| 37.06 | 237.8 |
| 42.43 | 285.1 |
| 56.67 | 89.4 |
| 58.30 | 82.9 | n=Atlox 3429. This emulsifier is a liquid blend of anionic and nonionic surfactants which is manufactured by ICI United States Incorporated and has the following gas chromatography characteristics:

| Retention time (min.) | Specific response |
| --- | --- |
| 2.23 | 103.6 |
| 3.34 | 5.8 |
| 16.47 | 168.4 |
| 23.84 | 72.4 |
| 33.89 | 176.9 |
| 38.72 | 70.7 |
| 42.74 | 65.5 |
| 46.21 | 30.6 |
| 56.90 | 126.6 | o=Emcol N 140-C. This emulsifier is a liquid blend of anionic and nonionic surfactants which is manufactured by Witco Chemical Corporation.

The "heavy aromatic naphtha" used in the evaluation of various emulsifiable concentrates of malathion has the following average composition and properties:

| Component | % by weight |
|---|---|
| Non-aromatics | 4.40 |
| ethylbenzene | 0.26 |
| o-xylene | 32.29 |
| m-xylene | 1.25 |
| p-xylene | 0.75 |
| 1,2-methyl-ethylbenzene | 5.05 |
| 1,3-methyl-ethylbenzene | 4.94 |
| 1,4-methyl-ethylbenzene | 17.71 |
| 1,2,3-trimethyl benzene | 3.62 |
| 1,2,4-trimethyl benzene | 22.45 |
| 1,3,5-trimethyl benzene | 6.53 |
| $C_{10}$ aromatics and heavier | 0.75 |
| | 100.00 |
| Properties | |
| Specific gravity (15.56/15.56° C.) | 0.853–0.875 |
| Flash point TCC min. °F. | 100 |
| Kauri-Butanol Value, min. | 92 |

Table I presents the results of several experiments evaluating various emulsifiable concentrates of malathion for emulsion stability and eye irritation.

data are summarized in Table III below. The emulsifying agents and the "heavy aromatic naphtha" herein below referred to are identified in Example 1.

TABLE II

Evaluation of the storage stability of emulsifiable concentrates of malathion as indicated by emulsion stability tests

| Formulation No | Percent by weight composition of formulations | | | | Emulsion stability + test | |
|---|---|---|---|---|---|---|
| | Malathion | Heavy aromatic naphtha | Emulsifiers A/% | B/% | Initial | 6 weeks at 45° C. |
| 1 | 62.5 | 30.5 | h/7.0 | — | P | F |
| 2 | 62.5 | 34.0 | h/3.5 | — | P | F |
| 3 | 62.5 | 34.0 | e/3.5 | — | F | F |
| 4 | 62.5 | 30.5 | a/4.2 | b/2.8 | P | P |
| 5 | 62.5 | 34.0 | a/2.1 | b/1.4 | P | F |
| 6 | 62.5 | 34.0 | c/0.7 | d/2.8 | P | F |
| 7 | 62.5 | 34.0 | m/1.4 | n/2.1 | P | F |

+Emulsion stability test: P = passed; F = failed

What is claimed is:

1. A low-eye-irritating emulsifiable insecticide concentrate composition comprising: on a weight basis, about 62.5% malathion; about 4.2% of a liquid blend of anionic and nonionic surfactants containing calcium and dodecylbenzene sulfonate, alkylphenoxy polyoxyethylene ethanols and polyalkylene glycol ether, having a specific gravity of 0.98 at 25° C., flash point (T.O.C. °F.) of 125, flash point (closed cup)=71° F., and a pH of 6.0–6.2, (TOXIMUL ®475); about 2.8% of a liquid blend of anionic and nonionic surfactants containing calcium dodecylbenzene sulfonate, alkylphenoxy polyoxyethylene ethonols and polyalkylene glycol ether, having a specific gravity of 1.001 at 25° C., flash point (T.O.C. °F.) of 125, flash point (closed cup)=68° F.; and pH of 5.0 (TOXIMUL ® 480); and about 30.5% heavy aromatic naphtha solvent.

2. An insecticidal emulsion comprising the composition of claim 1 and water.

TABLE I

Evaluation of emulsifiable concentrates of malathion for emulsion stability and eye irritation

| Formulation No | Percent by weight composition of formulations | | | | | Emulsion test + | | Eye irritation test ++ | Remarks |
|---|---|---|---|---|---|---|---|---|---|
| | Malathion | Xylene | heavy aromatic naphtha | Emulsifiers A/% | B/% | initial | 3 months | | |
| 1 | 62.0 | 31.0 | — | (a + b)/7.0 | — | — | — | R-11 | — |
| 2 | 62.2 | — | 34.3 | a/2.1 | b/1.4 | P | — | R-7 | — |
| 3 | 62.2 | — | 28.8 | a/4.2 | b/2.8 | P | — | R-7 | — |
| 4 | 62.1 | 30.9 | — | a/4.2 | b/2.8 | P | P | R-10 | — |
| 5 | 62.2 | 30.8 | — | a/4.2 | b/2.8 | P | P | R-10 | — |
| 6 | 62.2 | — | 30.8 | c11.4 | d/5.6 | — | — | I | — |
| 7 | 62.2 | — | 34.3 | c/0.7 | d/2.8 | F | — | R-7 | — |
| 8 | 62.0 | 31.0 | — | e/7.0 | — | — | — | I | — |
| 9 | 62.2 | 30.8 | — | e/7.0 | — | P | — | I | — |
| 10 | 62.2 | — | 34.3 | e/3.5 | — | F | — | R-7 | — |
| 11 | 62.1 | 30.9 | — | f/2.8 | g/4.2 | P | F | R-15 | — |
| 12 | 62.2 | — | 30.8 | h/7.0 | — | P | — | R-7 | — |
| 13 | 62.2 | — | 34.3 | h/3.5 | — | P | — | R-7 | — |
| 14 | 62.1 | 30.9 | — | i/6.0 | j/1.0 | P | F | I | — |
| 15 | 61.5 | 31.5 | — | m/2.8 | n/4.2 | — | — | I | — |
| 16 | 62.0 | 31.0 | — | (m + n)/7.0 | — | — | — | R-11 | — |
| 17 | 62.2 | — | 34.3 | m/1.4 | n/2.1 | P | — | R-7 | — |
| 18 | 62.2 | — | 32.9* | (k + l + n)/1.3 + 1.3 + 1.3 | — | F | — | I | *+1% acetic anhydride |
| 19 | 62.2 | — | 30.8 | m/2.8 | n/4.2 | P | — | R-14 | — |
| 20 | 62.0 | 31 | — | o/7.0 | — | — | — | I | — |

+Emulsion test: P = Passed; F = failed
++Eye irritation test: R = reversible eye damage; number refers to day required; e.g. R-11 reversible after 11 days. I = irreversible eye damage.

EXAMPLE 2

Preparation of emulsifiable concentrates of malathion for storage stability tests Varied amounts of malathion, a heavy aromatic naphtha and the selected emulsifiers are mixed and stirred until homogeneous. Emulsion stability tests are performed on fresh formulations using the procedure of Example 1. The formulations are then stored at 45° C. for six weeks and the tests are repeated. The composition of the samples and the obtained emulsion stability

* * * * *